United States Patent
Roberts et al.

(10) Patent No.: US 8,414,565 B2
(45) Date of Patent: Apr. 9, 2013

(54) PARAMETRIC MODEL BASED ABLATIVE SURGICAL SYSTEMS AND METHODS

(75) Inventors: Cynthia L. Roberts, Columbus, OH (US); Ashraf Mahmoud, Worthington, OH (US); Edward E Herderick, Pinkerington, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 10/539,181

(22) PCT Filed: Dec. 16, 2003

(86) PCT No.: PCT/US03/40302
§ 371 (c)(1),
(2), (4) Date: Jun. 2, 2006

(87) PCT Pub. No.: WO2004/058113
PCT Pub. Date: Jul. 15, 2004

(65) Prior Publication Data
US 2007/0073905 A1   Mar. 29, 2007

Related U.S. Application Data

(60) Provisional application No. 60/433,739, filed on Dec. 16, 2002.

(51) Int. Cl.
*A61B 18/20* (2006.01)
(52) U.S. Cl. .............................. 606/5; 128/898; 351/212
(58) Field of Classification Search ...... 606/5; 128/898; 351/212
See application file for complete search history.

(56) References Cited

U.S. PATENT DOCUMENTS

| | | | |
|---|---|---|---|
| 4,669,466 A | 6/1987 | L'Esperance | |
| 4,721,379 A | 1/1988 | L'Esperance | |
| 4,824,066 A | 4/1989 | Smith | |
| 4,856,513 A | 8/1989 | Muller | |
| 4,903,695 A | 2/1990 | Warner et al. | |
| 4,941,093 A | 7/1990 | Marshall et al. | |
| 5,098,426 A | 3/1992 | Sklar | |
| 5,613,965 A | 3/1997 | Muller | |
| 5,891,131 A * | 4/1999 | Rajan et al. ................. | 606/5 |
| 5,935,140 A | 8/1999 | Buratto | |

(Continued)

FOREIGN PATENT DOCUMENTS

| | | |
|---|---|---|
| EP | 1034756 A2 | 9/2003 |
| WO | 9111158 | 8/1991 |

(Continued)

OTHER PUBLICATIONS

Roberts et al., "The role of corneal biomechanics in customized ablative procedures," In MacRae S., Krueger R., Applegate R (eds). Customized Corneal Ablation. Thorofare, NJ; SLACK Incorporated. 2001.

(Continued)

*Primary Examiner* — Bill Thomson
*Assistant Examiner* — Jeffrey Lipitz
(74) *Attorney, Agent, or Firm* — Dinsmore & Shohl, LLP

(57) ABSTRACT

Example systems and methods for performing individually customized corneal ablative surgery is presented. The example systems and methods rely on a parametric model that correlates corneal measurements with predicted post-operative results and algorithm updates that facilitate achieving desired post-operative results.

12 Claims, 12 Drawing Sheets

U.S. PATENT DOCUMENTS

| | | | |
|---|---|---|---|
| 6,053,034 | A | 4/2000 | Tsui et al. |
| 6,056,740 | A | 5/2000 | Shimmick |
| 6,217,570 | B1 | 4/2001 | Nevyas |
| 6,280,435 | B1 | 8/2001 | Odrich et al. |
| 6,302,877 | B1 | 10/2001 | Ruiz et al. |
| 6,331,177 | B1 | 12/2001 | Munnerlyn et al. |
| 6,530,917 | B1 | 3/2003 | Seiler et al. |
| 6,547,393 | B2 | 4/2003 | Ruiz |
| 6,582,078 | B2 | 6/2003 | Halpern et al. |
| 6,685,663 | B2 | 2/2004 | Feinsod |
| 7,130,835 | B2 | 10/2006 | Cox |
| 2003/0208190 | A1 | 11/2003 | Roberts et al. |
| 2005/0096640 | A1* | 5/2005 | Dai et al. ............ 606/10 |
| 2005/0107775 | A1* | 5/2005 | Huang et al. ............ 606/5 |

FOREIGN PATENT DOCUMENTS

| | | |
|---|---|---|
| WO | 9316631 | 9/1993 |
| WO | 9418636 | 8/1994 |
| WO | 9853881 | 12/1998 |
| WO | 0128477 | 4/2001 |
| WO | 0177739 | 10/2001 |
| WO | 0207660 A | 1/2002 |
| WO | 02069787 | 9/2002 |
| WO | 03082162 A2 | 10/2003 |
| WO | 2004034928 A2 | 4/2004 |
| WO | 2004058113 A1 | 7/2004 |

OTHER PUBLICATIONS

Roberts, Corneal biomechanics and their role in corneal ablative procedures; Chapter Nine; pp. 109-131.

Roy P et al., Computational models of the effects of hydration on corneal biomechanics and the results of radial keratotomy, Journal of Biomechanical Engineering, Transactions of the ASME, vol. 118, 1996, p. 255-258.

Smolek MK et al., Interlamellar adhesive strength in human eye bank corneas. Invest Ophthalmol Vis Sci. 1990; 31:1087-1095.

Smolek MK, Interlamellar cohesive strength in the vertical median of human eye bank corneas, Invest Ophthalmol Vis Sci., 1993; 34:2962-2969.

Velinsky SA et al., On the computer-aided and optimal design of keratorefractive surgery, Refract Corneal Surg 1992; 8:173-182.

Veress AI et al., Biomechancial response of the cornea to photorefractive keratectomy, Investigative Ophthalmology and Visual Science Suppl., 1995, 36(4): S705.

Vito RP et al., A mechanical model of the cornea: the effects of physiological and surgical factors on radial keratotomy surgery, Refractive & Corneal Surgery, 1989, p. 82-88.

Von Kulajta et al., Posterior corneal astigmatism in a refractive surgery population poster (1999).

Anseth A et al., Polysaccharides in normal and pathologic corneas, Invest Ophthalmol Vis Sci 1962, 1:195-201.

Applegate RA et al., Corneal abberations, visual performance after radial keractectomy, Journal of Refractive Surgery, 14:397-407, 1998.

Applegate RA et al., Refractive surgery, optical aberrations, and visual performance, Journal of Refractive Surgery, 13:295-299, 1997.

Choi YI et al., Corneal flap dimensions in laser in situ keratomileusis using the Innovatome automatic microkeratome, 14 Korean J. Ophthalmol. 7-11 (2000) (Abstract).

Chongsiriwatana et al., Correction of surface tilt in intra-operative corneal topography poster (1998).

Dupps WJ et al., Geometric bias in PTK ablation profiles and associated keratometric changes in human globes, Investigative Ophthalmology and Visual Science Suppl, 1996, 37(3):S57.

Dupps WJ et al., Peripheral lamellar relaxation: a mechanism of induced corneal flattening in PTK and PRK? Investigative Ophthalmology and Visual Science Suppl, 1995, 36(4):S708.

Dupps WJ et al., Suppression of the acute biomechanical response to excimer laser keractectomy, Investigative Ophthalmology and Visual Science Suppl, 1999, 40(4):S110.

Hanna KD et al., Computer simulation of arcuate keratotomy for astigmatism, Refractive & Corneal Surgery, vol. 8, 1992, p. 152-163.

Katsube et al., A constitutive theory for porous composite materials, International Journal of Solids and Structures, vol. 35, pp. 4587-4596, 1998.

Katsube et al., The modified mixture theory for fluid-filled porous materials; theory, Journal of Applied Mechanics, Mar. 1987, vol. 54, pp. 35-40.

Katsube et al., The constitutive theory for fluid-filled porous materials, Journal of Applied Mechanics; 1985; 52:185-189.

Komai Y et al., The three-dimensional organization of collagen fibrils in the human cornea and sclera, Invest Ophthalmol Vis Sci.; 1991; 32: 2244-2258.

Munnerlyn CR et al., Photorefractive keratectomy: a technique for laser refractive surger, J Cataract Refract Surg. 1988; 14:46-52.

Oshika T et al., Comparison of corneal wavefront aberrations after photorefractive keratectomy and laser in situ keratomileusis, American Journal of Ophthalmology, 127:1-7, 1999.

Pinsky PM et al., A micro-structurally-based finite element mode of the incised human cornea, J Biomech 1991; 24:907-922.

Pinsky PM et al., Numerical modeling of radial, astigmatic, and hexagonal keratotomy, Refract Corneal Surg 192; 8:164-172.

Roberts C et al., poster presentation "Characterization of corneal curvature changes inside and outside the ablation zone in LASIK," May 3, 2000.

Roberts C, [Abstract] Characterization of corneal curvature changes inside and outside the ablation zone in LASIK, Investigative Ophthalmology and Visual Science Suppl. Mar. 15, 2000; 41(4):S679.

Notice of Allowance in U.S. Appl. No. 10/531,345, mailed Jun. 1, 2010 (4 pages).

Office Action in U.S. Appl. No. 10/332,891, mailed Apr. 28, 2010 (7 pages).

Office Action in U.S. Appl. No. 10/531,345, mailed Mar. 16, 2010 (6 pages).

Office Action in U.S. Appl. No. 10/531,345, mailed Sep. 15, 2009 (5 pages).

Office Action in U.S. Appl. No. 10/332,891, mailed Sep. 1, 2009 (5 pages).

Office Action in U.S. Appl. No. 10/531,345, mailed Jun. 1, 2009 (8 pages).

KR10-2005-7011101—Decision of Patent Grant (with translation), mailed Sep. 27, 2011 (3 pages).

EP03808464.6—Notice of Grant, mailed Nov. 2, 2011 (62 pages).

CA2,507,998 Office Action mailed Feb. 27, 2012 (3 pages).

Amm M et al., Refractive changes after phototherapeutic keratectomy, J Cataract Refract Surg. 1997; 23:839-844.

Biswell R, Cornea In: Vaughn DG, Asbury T, Riordan-Eva P, eds. General Ophthalmology. Norwalk, CT: Appleton & Lange, 1992: 125.

Bogan SJ et al., Classification of normal corneal topography based on computer-assisted videokeratography, Archives of Ophthalmology, 108(7):945-9, 1990.

Bryant MR et al., Finite element analysis of corneal topographic changes after excimer laser phototherapeutic keratectomy, Invest Ophthalmol Vis Sci 1993; 31 (suppl):804.

Bryant MR et al., Mathematical models of picosecond laser keratomileusis for high myopia, Journal of Refractive Surgery, vol. 16, 2000, p. 155-162.

Campos M et al., Clinical follow-up of phototherapeutic keratectomy for treatment of corneal opacities, Am J Ophthalmol. 1993; 115:433-440.

Dierick HG et al., Is the corneal contour influenced by a tension in the superficial epithelial cells? A new hypothesis, Refract Corneal Surg 1992; 8:54-59, Comments in: Refract Corneal Surg 1992; 8:60 and 1993; 9:147.

Dupps WJ, Chemo-mechanical modification of the corneal response to photokeratomy [dissertation]. Columbus (OH): The Ohio State University, 1998.

Dupps WJ, Peripheral stromal expansion and anterior corneal flattening in phototherapeutic keratectomy: an in vitro human study [thesis], Columbus (OH): The Ohio State University, 1995.

Ehlers N, Studies on the hydration of the cornea with special reference to the acid hydration, Acta Ophthalmol. 1966; 44:924-925.

Ehlers N, The fibrillary texture and the hydration of the cornea, Acta Ophthalmol 1966; 44:620-630.

Fagerholm P et al., Phototherapeutic keratectomy: long-term results in 166 eyes, Refract Corneal Surg. 1993; 9(suppl): S76-81.

Fand AK, Effects of phototherapeutic keratectomy on perifpheral corneal thickness [ARVO Abstract], Invest Ophthalmol Vis Sci.1996; 37(3):S568 nr 2609.

Gartry D et al., Excimer laser treatment of corneal surface pathology: a laboratory and clinical study, Br J Ophthalmol. 1991; 75:258-269.

Gilbert ML et al., Corneal flattening by shallow circular trephination in human eye bank eyes, Refract Corneal Surg 1990; 6:113-116.

Gilbert ML et al., Human corneal steepening by annular keratotomy, Invest Ophthalmol Vis Sci1989; 30(suppl):186.

Hahn TW et al., Phototherapeutic keratectomy in 9 eyes with superficial corneal diseases, Refract Corneal Surg. 1993; 9(suppl): S115-118.

Hanna KD et al., Preliminary computer simulation of the effects of radial keratotomy, Arch Ophthalmol 1989; 107:911-918.

Hedbys BO et al., A new method for the determination of the swelling pressure of the corneal stroma in vitro, Exp Eye Res 1963; 2:122-129.

Hedbys BO et al., Flow of water in the corneal stroma, Exp Eye Res 1962; 1:262-275.

Hedbys BO et al., The imbibation pressure of the corneal stroma, Exp Eye Res 1963; 2:99-111.

Hee MR et al., Quantitative assessment of macular edema with optical coherence tomography, Arch Ophthalmology 1995; 113: 1019-1029.

Hee MR et al., Optical coherence tomography for ophthalmic imaging, IEEE Engineering in Medicine and Biiology 1995; 14: 67-76.

Hee MR et al., Topography of diabetic macular edema with optical coherence tomography, Ophthalmology, 1998, vol. 15, 2: 360-370.

Hersh PS et al., Phototherapeutic keratectomy: strategies and results in 12 eyes, Refract Corneal Surg. 1993; 9 (suppl):S90-95.

Hjortdal JO, Region elastic performance of the human cornea, Journal of Biomechanics (1996) 29, 931-942.

Huang D et al., Optical coherence tomography, Science 1991; 254: 1178-1181.

Izatt, J et al., Micrometer-Scale Resolution Imgaing of the Anterior Eye in Vivo with Optical Coherence Tomography, Arch Opthalmol, vol. 112, Dec. 1994 (6 pages).

Jakus MA, The fine structure of the human cornea, In: Smelser GK, ed, The Structure of the Eye, New York, NY: Academic Press, 1961.

Jue B, et al., The mechanical properties of the rabbit and human cornea, J Biomechanics 1986; 19:847-853.

Kanai A et al., Electron microscopic studies of swollen corneal stroma, Ann Ophthalmol 1973; 5:178-190.

Klyce SD et al., In vivo determination or corneal swelling pressure, Exp EyeRes 1971; 11:220-229.

Koers DM, The measurement of human corneal thickness by photography [master's thesis]. Columbus, OH: The Ohio State University; 1982.

Lembach, poster presentation, The Refractive Effect of the Flap in Laser in situ keratomileusus (LASIK), 2001.

Lindstrom RL et al., Six-month results of hyperopic and stigmatic LASIK in eyes with primary and secondary hyperopia, Tr Am Ophth Soc 1999, XCVII:241-260.

Litwin KL et al., Changes in corneal curvature at different excimer laser ablative depths, Am J Ophthalmol. 1991; 111:382-384.

MacRae SM et al., Large optical zone ablation treatment of myopia in the Oregon-Kansas study, Investigative Ophthalmology and Visual Sciences Suppl. 1999; 40(4):S588. [Abstract #3087].

Mahmoud AM et al., poster presentation, The Ohio State University Corneal Topography Tool. Abstract, Invest Ophthalmol Vis Sci 2000; 41:S677.

Maloney RK, A prototype erodible mask delivery system for the excimer laser, Ophthalmology 1993; 100:542-549.

Marshall J et al., An untrastructural study of corneal incisions induced by an excimer laser at 193 nm, Ophthalmol 1985; 92:749-758.

Maurice DM et al, Cohesive strength of corneal lamellae, Exp Eye Res 1990; 50:59-63.

Maurice DM, The cornea and sclera. In: Dayson H, ed, The eye. vol. 1b: vegetative physiology and biochemistry. Orlando, FL: Academic Press, 1984:1-158.

Maurice DM, The movement of fluorescein and water in the cornea, Am J Ophthalmol 1960; 49:1011-1019.

McDonald MB et al., "Autonomous custom cornea LASIK," First International Congress of Wavefront Sensing and Aberration Free Ablative Corrections, Optical Society of America Annual Meeting, 2000 (Non-archived Presentation; partial summary of presented material provided).

McDonnell PJ et al., Phototherapeutic keratectomy with excimer laser for Reis-Buckler's corneal dystrophy, Refract Corneal Surg. 1992; 8:306-310.

Mishima S et al., The effect of normal evaporation on the eye, Exp Eye Res 1961; 1:46-52.

Mishima S et al., The permeability of the corneal epithelium and endothelium to water, Exp Eye Res 1967; 6:10-32.

Munger R et al., "Ablation profile and epithelial regrowth after myopic PRK with VISX Star," American Society of Cataract and Refractive Surgery Annual Meeting, 1999 (Non-archived Presentation; partial summary of presented material provided).

O'Brart DPS et al., Treatment of band keratopathy by excimer laser phototherapeutic keratectomy: surgical techniques and long term follow up, Br J Ophthalmol. 1993; 77:702-708.

Örndahl M et al., Treatment of corneal dystrophies with excimer laser, Acta Ophthalmol. 1994; 72:235-240.

Pinsky PM et al., A microstructurally-based mechanical model of the human cornea with application to keratotomy, Invest Ophthalmol Vis Sci 1994; 31 (suppl): 1296.

Polack FM, Morphology of the cornea, I: study with silver stains, Am J Ophthalmol. 1961; 51:179.

Reinstein DZ et al., Very high-frequency ultrasound corneal analysis identifies anatomic correlates of optical complications of lamellar refractive surgery: anatomic diagnosis in lamellar surgery, Ophthalmology, 1999, 106(3): 474-82.

Reinstein DZ et al., Arc-scanning very high-frequency digital ultrasound for 3D pachymetric mapping of the corneal epithelium and stroma in laser in situ keratomileusis, Journal of Refractive Surgery, vol. 16, Jul./Aug. 2000 (pp. 414-430).

Roberts, "Customization and Corneal Response," Bausch & Lomb Refractive Alliance, held in conjunction with the American Academy of Ophthalmology, Dallas, Texas, Oct. 22, 2000.

Roberts, Future challenges to aberration-free ablative procedures, Journal of Refractive Surgery, vol. 16, S623-S629, Sep./Oct. 2000.

Roberts, The cornea is not a piece of plastic, editorial, Journal of Refractive Surgery, vol. 16, Jul./Aug. 2000.

Rogers et al., Phototherapeutic keratectomy for Reis Bucklers' corneal dystrophy, Austral N Zealand J Ophthalmol. 1993; 21:247-250.

Sborgia et al., "Corneal interactived programmed topographic ablation: preliminary results," American Society of Cataract and Refractive Surgery Annual Meeting, 1999 (Non-archived Presentation; partial summary of presented material provided).

Seiler T, "Der excimer-laser: ein instrument fur die hornhautchirurgie," Der Ophthalmologe. 1992; 89:128-133 (Reference not available; partial summary of material therein provided).

Seiler TS et al., Does Bowman's layer determine the biomechanical properties of the cornea? Refract Corneal Surg1992; 8:139-142.

Sher NA et al., Clinical use of the 193-nm excimer laser in the treatment of corneal scars, Arch Ophthalmol. 1991; 109:491-498.

Shin TJ et al., The distribution of strain in the human cornea (1997) 30, 497-503.

Spoerl E, The swelling behaviour of the cornea after artificial cross-linking. ARVO abstracts, Invest Ophthalmol Vis Sci1997; 38:S507.

Stark W et al., Clinical follow-up of 193-nm ArF excimer laser photokeratectomy, Ophthalmol. 1992; 99:805-812.

Starr MS et al., Excimer laser phototherapeutic keratectomy, Cornea 1996; 15:557-565.

Thompson VM, Excimer laser phototherapeutic keratectomy: clinical and surgical aspects, Ophthalmic Surg & Lasers 1995; 26:461-472.

Waring GO III, Corneal structure and pathophysiology. In: Leibowits HM, ed. Corneal disorders: clinical diagnosis and management, Philadephia, PA: WB Saunders, 1984:3-25.

Ytteborg J et al., Corneal edema and intraocular pressure II Clinical results, Arch Ophthalmol 1965; 74:375-381.

U.S. Appl. No. 10/531,345—Notice of Allowance, mailed Dec. 16, 2010 (4 pages).
U.S. Appl. No. 10/531,345—Notice of Allowance, mailed Apr. 1, 2011 (5 pages).
U.S. Appl. No. 10/531,345—Notice of Allowance, mailed May 25, 2011 (5 pages).

Office Action in CA 2,507,998, mailed Oct. 16, 2012.
Tham, M., "Overview of Mechanistic Modelling Techniques," Dept. Chem. Proc. Engr., Univ Newcastle Upon Tyne (1998-2000).

* cited by examiner

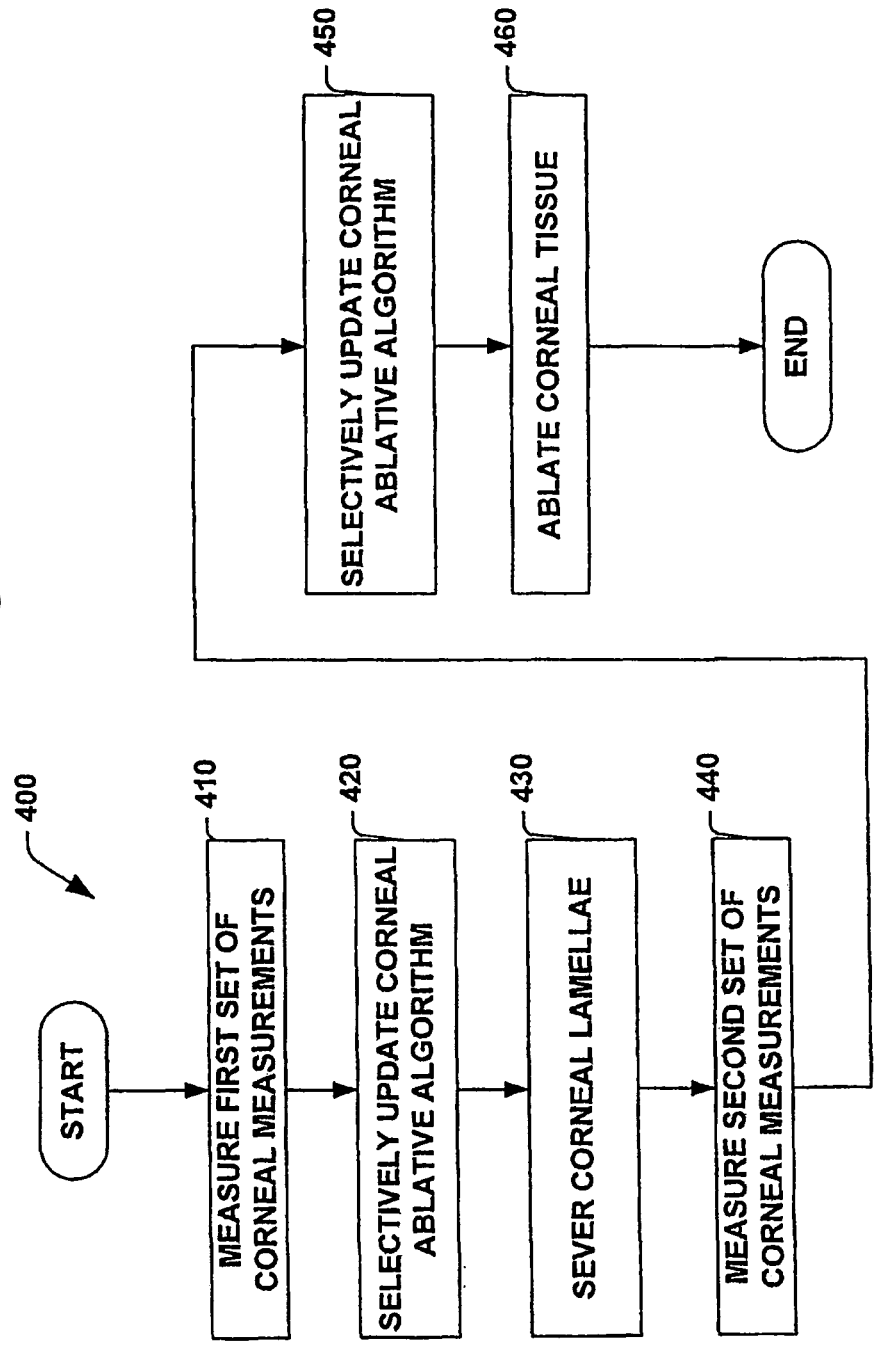

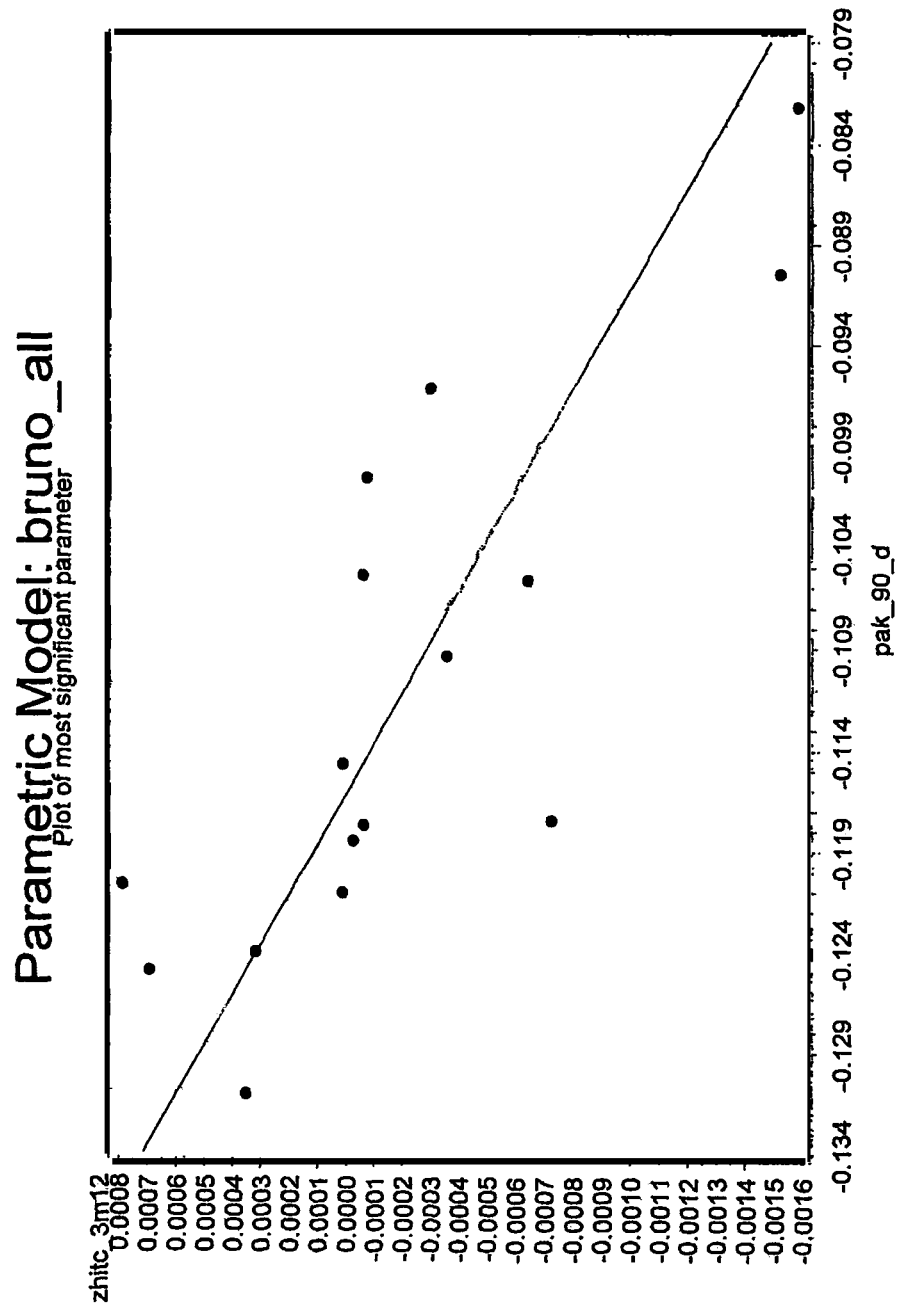

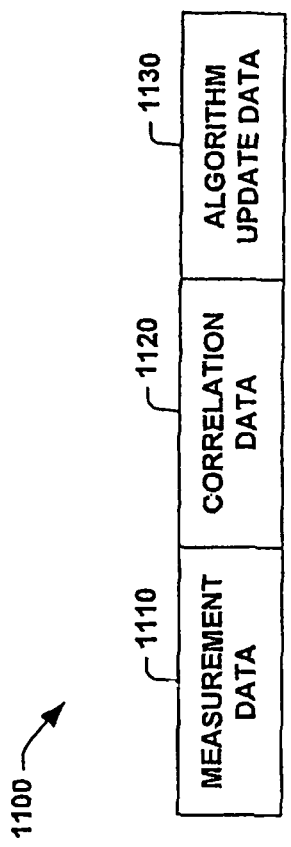

PARAMETRIC MODEL BASED ABLATIVE SURGICAL SYSTEMS AND METHODS

CROSS-REFERENCE TO RELATED APPLICATIONS

This application is the National Stage Entry of International Application No. PCT/US2003/040302 filed Dec. 16, 2003, which claims the benefit of U.S. Provisional Application Ser. No. 60/433,739, filed Dec. 16, 2002.

The methods, systems, computer readable media and so on described herein relate generally to eye surgery related computer programming and more particularly to updating a corneal ablative algorithm based on correlations between pre-operative measurements and predicted post-operative results as modeled in a parametric model.

More than one million laser refractive surgeries based on a mean population response eye are performed every year to correct myopia. Of the many individuals treated with conventional procedures, about 15% to 50% do not achieve 20/20 vision due, at least in part, to the relationship of the patient eye to the mean population response eye and the dependence of refractive procedures on the mean population response eye. Additionally, many individuals cannot benefit from corneal ablative techniques because their eyes do not fall within parameters modeled by the mean population response eye. Although a greater percentage of individuals treated with customized or wavefront guided procedures achieve 20/20 vision than with conventional procedures, visual aberrations are still induced in a significant number of patients, which degrade vision from the planned outcome of a reduction in aberrations over the pre-operative state.

Initial attempts at photorefractive keratectomy (PRK) used a model presented in 1988 by Munnerlyn, et al. The cornea was modeled as two refracting surfaces with a bulk material in between the two refracting surfaces where there was a known index of refraction. In treating myopia, the goal was to increase the anterior radius of curvature, thus decreasing the curvature and thus power of the anterior surface as illustrated in FIG. 1. A simple geometric formula resulted, which assumed the targeted corneal shape was a function of the ablation profile. This is the "shape subtraction" paradigm, based on a geometric approach to tissue removal and secondary curvature change, where the final corneal shape is assumed to be determined by how much tissue is subtracted by a laser. Essentially, this model treats the cornea as a piece of plastic to be sculpted into an ideal surface shape by laser ablation.

The equations described by Munnerlyn, et al. still serve as a starting point for ablation algorithms. However, PRK, Laser Epithelial Keratomileusis (LASEK), and Laser Assisted in-Situ Keratomileusis (LASEK) fail to consistently produce expected refractive outcomes.

The following presents a simplified summary of methods, systems, and computer readable media employed to customize ablative algorithms based on a parametric model that correlates measurements taken pre-operatively and/or during surgery with predicted post-operative results to facilitate providing a basic understanding of these items. This summary is not an extensive overview and is not intended to identify key or critical elements of the methods, systems, and computer readable media or to delineate the scope of these items. This summary provides a conceptual introduction in a simplified form as a prelude to the more detailed description that is presented later.

This application concerns updating an ablative algorithm based on individual measurements taken before and/or during surgery. The measurements have been correlated with desired predicted post-operative results. Example measurements include, but are not limited to, modulus of elasticity, corneal acoustic response to ultrasonic excitation, pachymetric profile in multiple meridians, pachymetric asymmetry between vertical and horizontal meridians, magnitude of difference in pachymetry between center and periphery, corneal width, anterior chamber angle and depth, corneal curvature profile in multiple meridians, magnitude of astigmatism, difference in astigmatism between center and periphery topographic response to the cutting of a LASIK flap. Example correlations include, but are not limited to, greater peripheral thickness causing greater spherical aberration. For example, measuring peripheral thickness facilitates predicting post-operative spherical aberration, thus a peripheral thickness measurement in the range {a, b} suggests (taking action to increase peripheral ablation, diminishing post-operative spherical aberration).

Over time, the response of a cornea to ablative surgery (e.g., LASEK, PRK, LASIK) has been studied. Of a large number of parameters available to measure a cornea, mathematical techniques identified correlations between certain pre-operative measurements and predicted post-operative results. Thus, customized and customizable corneal ablative systems and methods that benefit from the studies and correlations were developed. The corneal ablative systems and methods depart from conventional ablative techniques that treat the corneal as a piece of plastic and/or that do not consider individual parameters (e.g., modulus of elasticity). Example parameters for which correlations were made include, but are not limited to, modulus of elasticity, corneal acoustic response to ultrasonic excitation, pachymetric profile in multiple meridians, pachymetric asymmetry between vertical and horizontal meridians, magnitude of difference in pachymetry between center and periphery, corneal width, anterior chamber angle and depth, corneal curvature profile in multiple meridians, magnitude of astigmatism, difference in astigmatism between center and periphery topographic response to the cutting of a LASIK flap. Thus, LASEK, LASIK and/or PRK procedures can be improved by taking pre-operative measurements of the eye, and choosing and/or customizing an ablation algorithm based on correlations in a parametric model. In LASIK, in addition to pre-operative measurements, measurements taken during a surgical procedure facilitate further customizing the ablation algorithm.

Certain illustrative example methods, systems, and computer readable media are described herein in connection with the following description and the annexed drawings. These examples are indicative, however, of but a few of the various ways in which the principles of the methods, systems, computer readable media and so on may be employed and thus are intended to be inclusive of equivalents. Other advantages and novel features may become apparent from the following detailed description when considered in conjunction with the drawings.

FIG. 4 illustrates another example parametric model method.

FIG. 4a illustrates a regression analysis.

Figure 5:
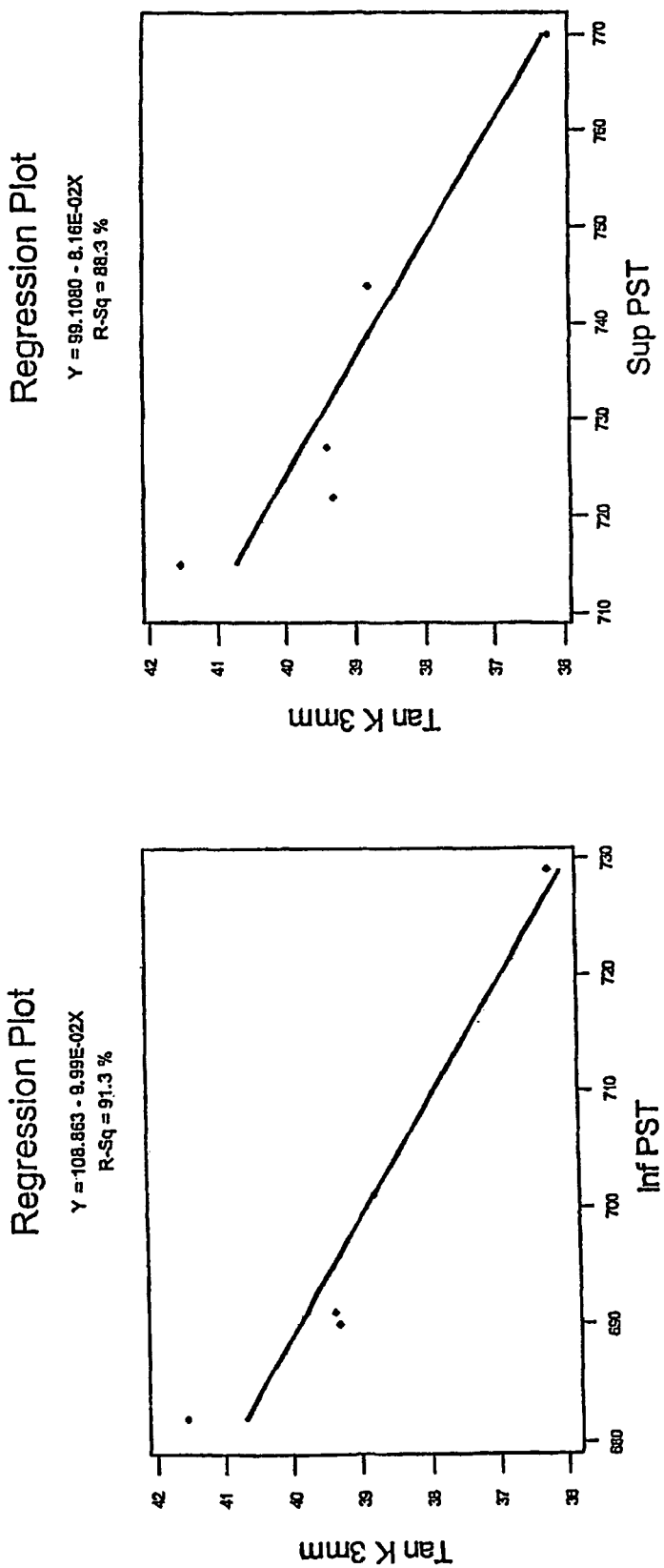

FIG. 5 presents a regression analysis of peripheral stromal thickness of the superior region (left plot) and the inferior region (right plot) against curvature.

Figure 6:
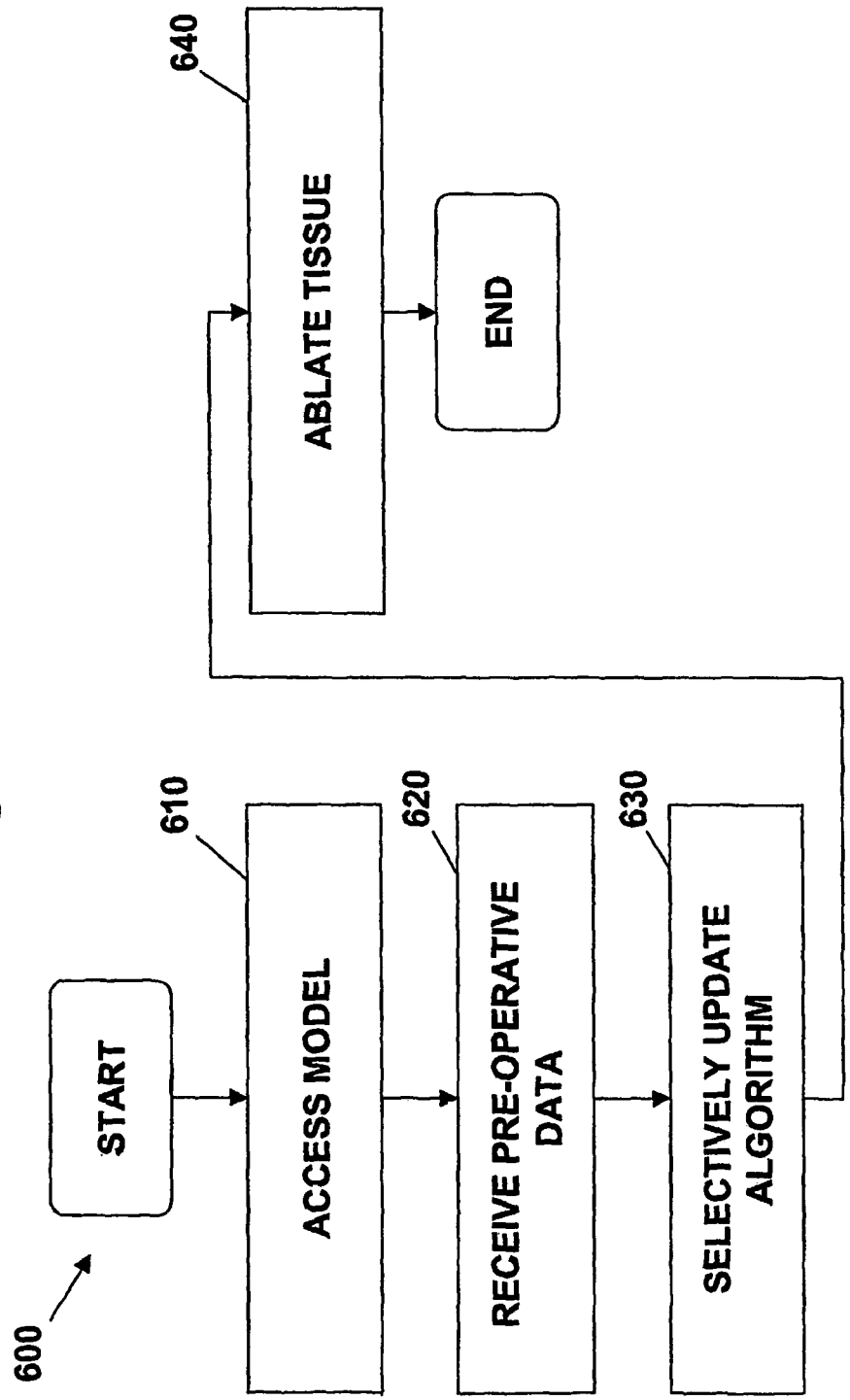

FIG. 6 is a flowchart of an example PRK and/or LASEK surgical technique.

Figure 7:
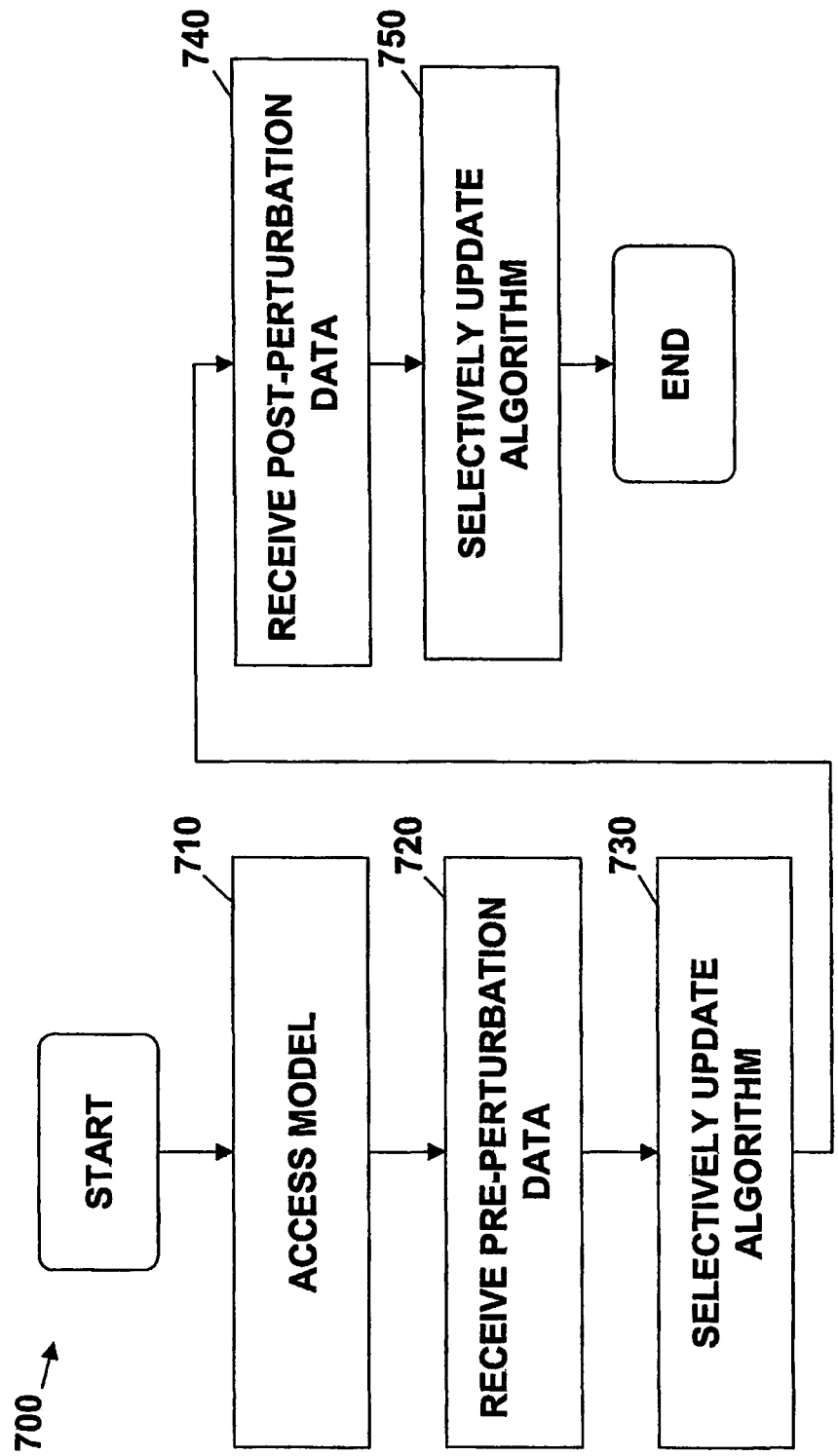

FIG. 7 is a flowchart of an example LASIK surgical technique.

Figure 8:
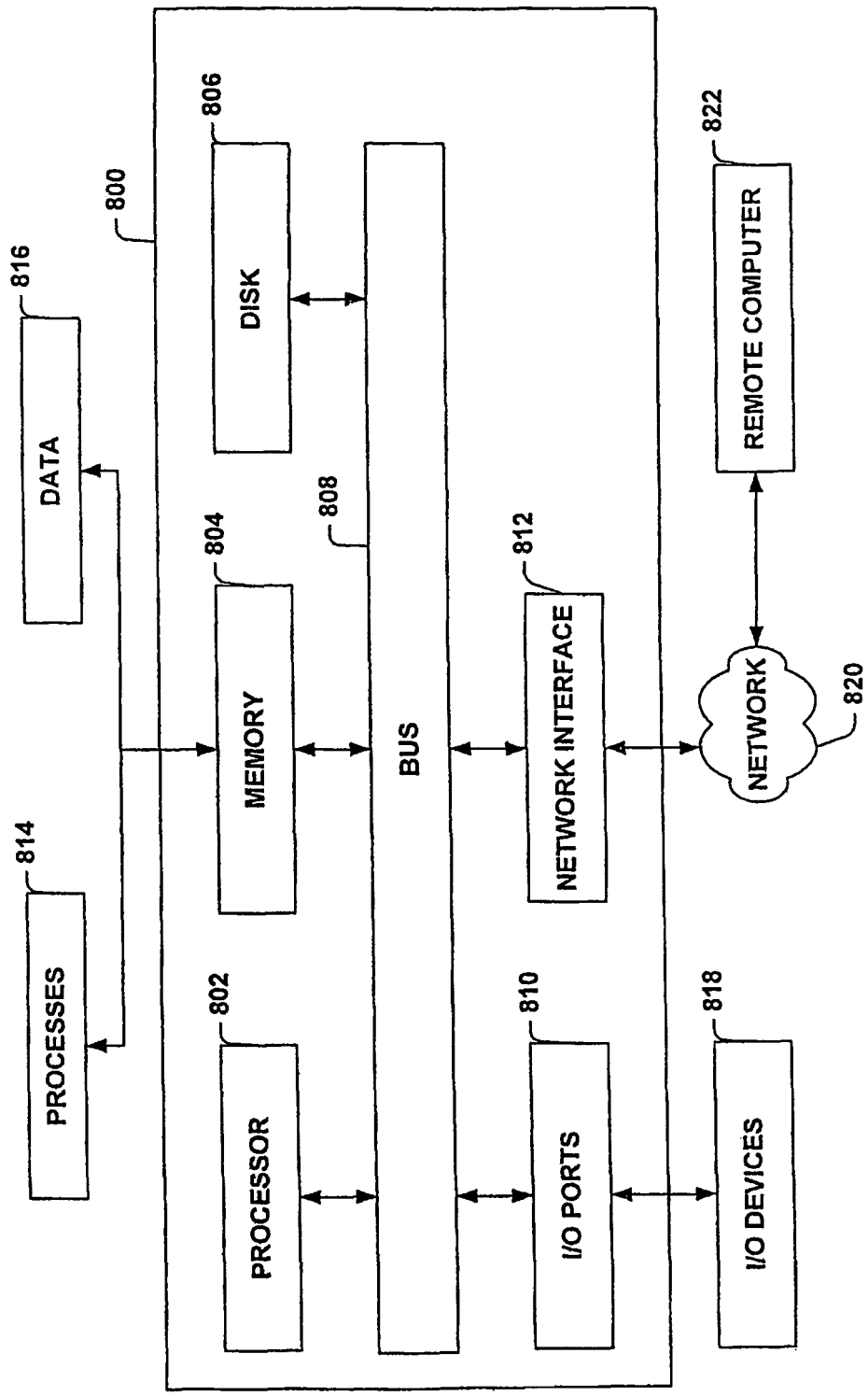

FIG. 8 is a schematic block diagram of an example computing environment with which the example methods and systems described herein can interact.

Figure 9:
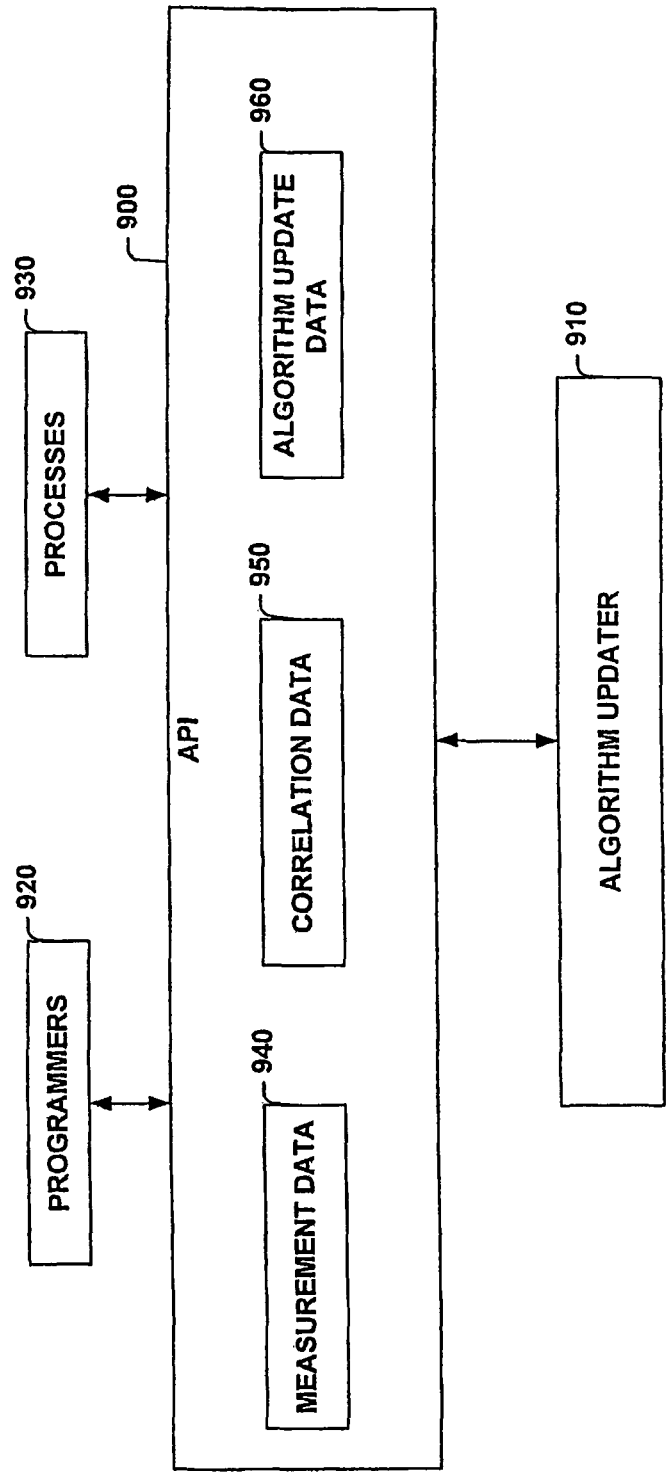

FIG. 9 illustrates an API.

Figure 10:
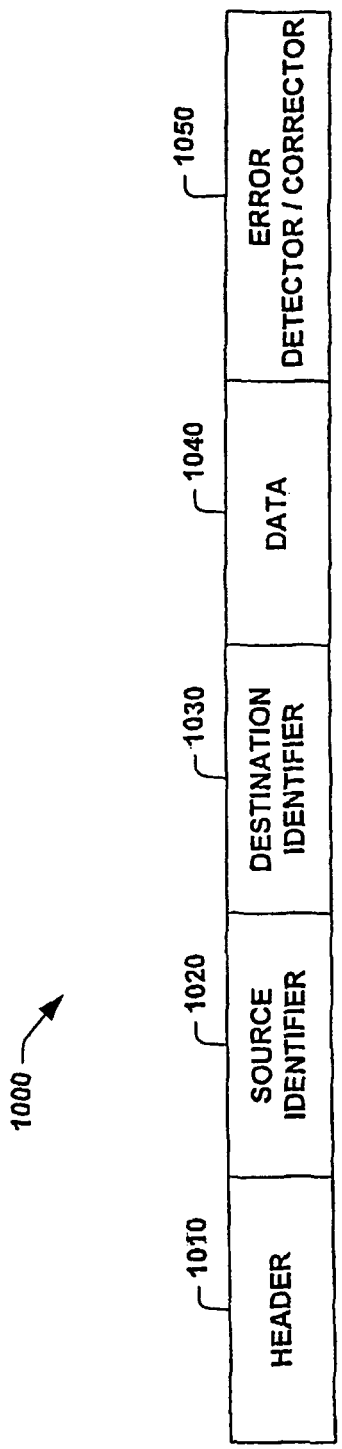

FIG. 10 illustrates a data packet.

FIG. 11 illustrates subfields in a data packet.

Example methods, systems, and computer media are now described with reference to the drawings, where like reference numerals are used to refer to like elements throughout. In the following description, for purposes of explanation, numerous specific details are set forth in order to facilitate thoroughly understanding the methods, systems, computer readable media and so on. It may be evident, however, that the methods, systems and computer readable media can be practiced without these specific details. In other instances, well-known structures and devices are shown in block diagram form in order to simplify description.

As used in this application, the term "computer component" refers to a computer-related entity, either hardware, firmware, software, a combination thereof, or software in execution. For example, a computer component can be, but is not limited to being, a process running on a processor, a processor, an object, an executable, a thread of execution, a program and a computer. By way of illustration, both an application running on a server and the server can be computer components. One or more computer components can reside within a process and/or thread of execution and a computer component can be localized on one computer and/or distributed between two or more computers.

"Signal", as used herein, includes but is not limited to one or more electrical or optical signals, analog or digital, one or more computer instructions, a bit or bit stream, or the like.

"Software", as used herein, includes but is not limited to, one or more computer readable and/or executable instructions that cause a computer or other electronic device to perform functions, actions and/or behave in a desired manner. The instructions may be embodied in various forms like routines, algorithms, modules, methods, threads, and/or programs. Software may also be implemented in a variety of executable and/or loadable forms including, but not limited to, a stand-alone program, a function call (local and/or remote), a servelet, an applet, instructions stored in a memory, part of an operating system or browser, and the like. It is to be appreciated that the computer readable and/or executable instructions can be located in one computer component and/or distributed between two or more communicating, co-operating, and/or parallel processing computer components and thus can be loaded and/or executed in serial, parallel, massively parallel and other manners.

Figure 1:
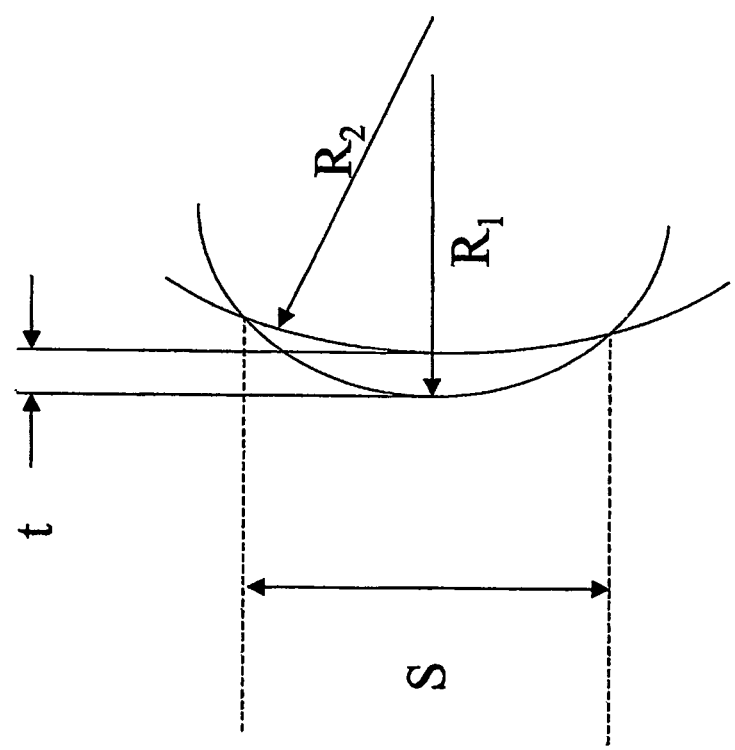
FIG. 1 illustrates a shape subtraction model.

FIG. 1 is a schematic of the simple "shape-subtraction" paradigm for correcting myopia. $R_1$ and $R_2$ are initial and final radii of curvature, t is the maximum depth of the laser cut, and s is the diameter of the optical zone. While the shape subtraction model has yielded satisfactory results without considering correlations between pre-operative measurements (and/or measurements taken surgery) and post-operative results, ablative techniques may benefit from such measurements and correlations. For example, Table 1 presents errors encountered in elevation and curvature using conventional techniques.

TABLE 1

| Error between Predicted and Measured Topography after LASIK | | |
|---|---|---|
| | elevation<br>mean ± sd (n = 10)<br>RMS error | curvature<br>mean ± sd (n = 10)<br>RMS error |
| central 4 mm diameter | 18 ± 14 microns | 4.92 ± 1.89 diopters |
| 4-9 mm diameter zone | 23 ± 11 microns | 8.06 ± 1.76 diopters |
| overall | 22 ± 11 microns | 6.85 ± 1.50 diopters |

In LASIK procedures, a flap is cut with a microkeratotone to a thickness of approximately 160 microns. Biomechanically, this approximates a 160-micron depth severing of corneal lamellae, similar to an ablation, except no tissue is removed. The amount of corneal flattening produced by the flap cut predicts certain post-operative results. Analyzing topography of the epithelial surface of the cornea, before and after cutting the flap, permits identifying correlations between the topography and certain post-operative results. Thus, this application describes example systems and methods that facilitate updating an ablative algorithm based, at least in part, on correlations associated with corneal measurements taken before and/or after cutting a LASIK flap.

To facilitate identifying correlations between pre-operative measurements and/or measurements taken during surgery and predicted post-operative results, and to facilitate building the parametric model, a study was conducted on 2380 patients who received LASIK. The patients had corneal topography measurements taken pre-operatively and post-operatively.

Correlations were also identified by in vitro studies. In one study, fourteen de-epitheliazed eye bank globes from seven donors were subjected in paired control fashion to either broad beam PTK or sham photoablation. Changes in anterior curvature were measured by autokeratometry. Changes in stromal thickness in the vertical meridian were measured using corneal optical section image analysis. The corneal cross section was divided into five regions for analysis, far superior, near superior, central, near inferior, and far inferior. Analysis included evaluating peripheral thickness changes in geometric bias as predictors of curvature change. Geometric bias was defined as either a myopic or a hyperopic bias in the pattern of ablation zone thickness loss in order to investigate shape subtraction theories of hyperopic shift in PTK.

Results of this study demonstrated that photoablation caused reductions in keratometric curvature (−6.28+/−3.23 D, p=0.002) relative to untreated paired controls. The mean keratometric shift measured during sham PTK was not significantly different from zero (+0.31+/−0.85 D, p=0.38). In addition to flattening the spherical curvature component, ablated corneas demonstrated higher absolute magnitudes of keratometric cylinder (2.98+/−0.88 D) than controls (0.46+/−1.72 D, p=0.009), indicating a biomechanical component to the induced cylinder. The relative peripheral stromal thickness change, expressed as the mean pair wise difference (PTK-control), was +57.3+/−42.8 μm (p=0.01) or +8.5+/−5.7% (p=0.1), demonstrating thickening relative to controls. Central curvature shifts were linearly dependent upon regional peripheral stromal thickness changes in ablated and control eyes. Thus, further correlations were identified.

Another in vitro study further examined the relationship between peripheral stromal thickening and central flattening. A paired control human donor eye study (n=20) assessed pre-operative topical glutaraldehyde (GTA) treatment as a technique for inhibiting PTK induced peripheral stromal thickening and for attenuating the acute corneal flattening response. Eyes were individually mounted in a custom holder, inflated to normal intraocular pressure (about 15 mmHg) and de-epithelialized. One cornea of a given donor was immersed in a 15% dextran solution for 40 minutes and transferred to 4% GTA/dextran for an additional 20 minutes. The fellow control was exposed to 15% dextran for 60 minutes. The eyes were subsequently subjected to (1) sham PTK, a same eye control phase incorporated to account for thinning due to intraoperative dehydration, (2) PTK (5 mm diameter, 100 μm depth) and (3) a one hour hypo-osmotic soak phase designed to assess the anti-swelling activity of stromal cross-linking. A scanning slit topography system (Orbscan) was employed to acquire triplicate thickness and curvature measurements before and after experimental phases. Cross-linking inhibited peripheral stromal thickening during PTK and postoperative hypo-osmotic immersion. In addition, during PTK, cross-linked corneas demonstrated 36% less hyperopic shift relative to paired controls (p=0.001). The magnitude of this latter effect was linearly dependent upon the magnitude of cross-link mediated suppression of the peripheral thickening response to PTK (r=0.68, p=0.03). Thus, acute hyperopic shifts in a donor model of PTK can be reduced through pre-operative application of a collagen cross-linking reagent. Thus, example systems and methods described herein rely, at least in part, on correlations associated with this study.

A retrospective analysis of a refractive surgery dataset was performed. The purpose of this analysis was two fold. A first purpose was to demonstrate the ability to perform data analysis on a large set of independent parameters extracted from preoperative clinical data. A second purpose was to seek preliminary confirmation of the biomechanical response model by analyzing refractive surgery outcomes and their statistical relationship to preoperative measured parameters, which was hypothesized to likely influence this response. The dataset used for this preliminary study was based upon a database created from an examination of 18 eyes of 9 patients measured preoperatively with an Orbscan II corneal topography system, at one day, one week, one month and three months after receiving LASIK with a Summit Apex Plus excimer laser. Nearly 200 preoperative parameters were calculated based on data extracted from the Orbscan topographies. These pre-operative parameters consisted of indices related to individual corneal geometries such as shape, pachymetry profiles in multiple meridians, white-to-white measurement of corneal size, anterior chamber depth, as well as surface curvature parameters. All 200 parameters were included as independent variables in a stepwise multiple linear regression analysis to determine which were significant predictors of the dependent post-operative outcome parameters. Outcome parameters included visual function parameters, such as spherical equivalent refraction, as well as outcome shape parameters based on a Zernike decomposition of the anterior surface elevation topography, measured at 3 months post-operatively.

Shown in Table 2 is the outcome of the stepwise regression with Zernike term #12 ($Z_{12}$) from the anterior surface elevation as the dependent outcome variable. $Z_{12}$ is the term related to spherical aberration, which has been shown to be significantly increased after refractive surgery. The independent pre-operative parameters in table 2 are ranked based on their partial $R^2$ value. The strongest pre-operative predictor of post-operative $Z_{12}$ in the topographic Zernike decomposition was an index labeled pak_90_d. This index represents the difference between the central pachymetry and the peripheral pachymetry in a sector around the 90-degree meridian. This single variable accounts for approximately 66% of the variability in post-operative $Z_{12}$.

TABLE 2

| Step | Variable Entered | Number Vars In | Partial R-Square | Model R-Square | F Value | Pr > F |
|---|---|---|---|---|---|---|
| 1 | pak_90_d | 1 | 0.6626 | 0.6626 | 27.49 | 0.0001 |
| 2 | srax_pak_pr | 2 | 0.1018 | 0.7644 | 5.62 | 0.0339 |
| 3 | osi_ref_pr | 3 | 0.0972 | 0.8616 | 8.42 | 0.0133 |
| 4 | ww | 4 | 0.048 | 0.9095 | 5.83 | 0.0343 |
| 5 | ti_ref_pr | 5 | 0.0307 | 0.9402 | 5.14 | 0.0468 |
| 6 | ti_tan_pr | 6 | 0.0202 | 0.9605 | 4.61 | 0.0603 |
| 7 | tano_0_pr | 7 | 0.0302 | 0.9907 | 26 | 0.0009 |
| 8 | hormwb5_pr | 8 | 0.0062 | 0.9969 | 13.95 | 0.0073 |
| 9 | dsi_ref_pr | 9 | 0.002 | 0.9989 | 10.73 | 0.0169 |
| 10 | acd | 10 | 0.0008 | 0.9997 | 11.9 | 0.0183 |
| 11 | csi_pak_pr | 11 | 0.0003 | 1 | 30.8 | 0.0052 |
| 12 | refo_pr | 12 | 0 | 1 | 16.75 | 0.0264 |
| 13 | hormzc5_pr | 13 | 0 | 1 | 36.2 | 0.0265 |
| 14 | dsi_tan_pr | 14 | 0 | 1 | 18578.2 | 0.0047 |

The regression plot of parameter pak_90_d (difference between the central pachymetry and the peripheral pachymetry around the 90 degree meridian) and Zernike term #12 is shown in FIG. 4a. The second strongest predictor of $Z_{12}$ was srax_pak_pr, which is another pachymetric profile index. This predictor calculates the angle between the thickest meridian above 180 degrees and the thickest meridian below 180 degrees. The two-parameter model accounts for 76% of the variability in the outcome variable.

Figure 2:
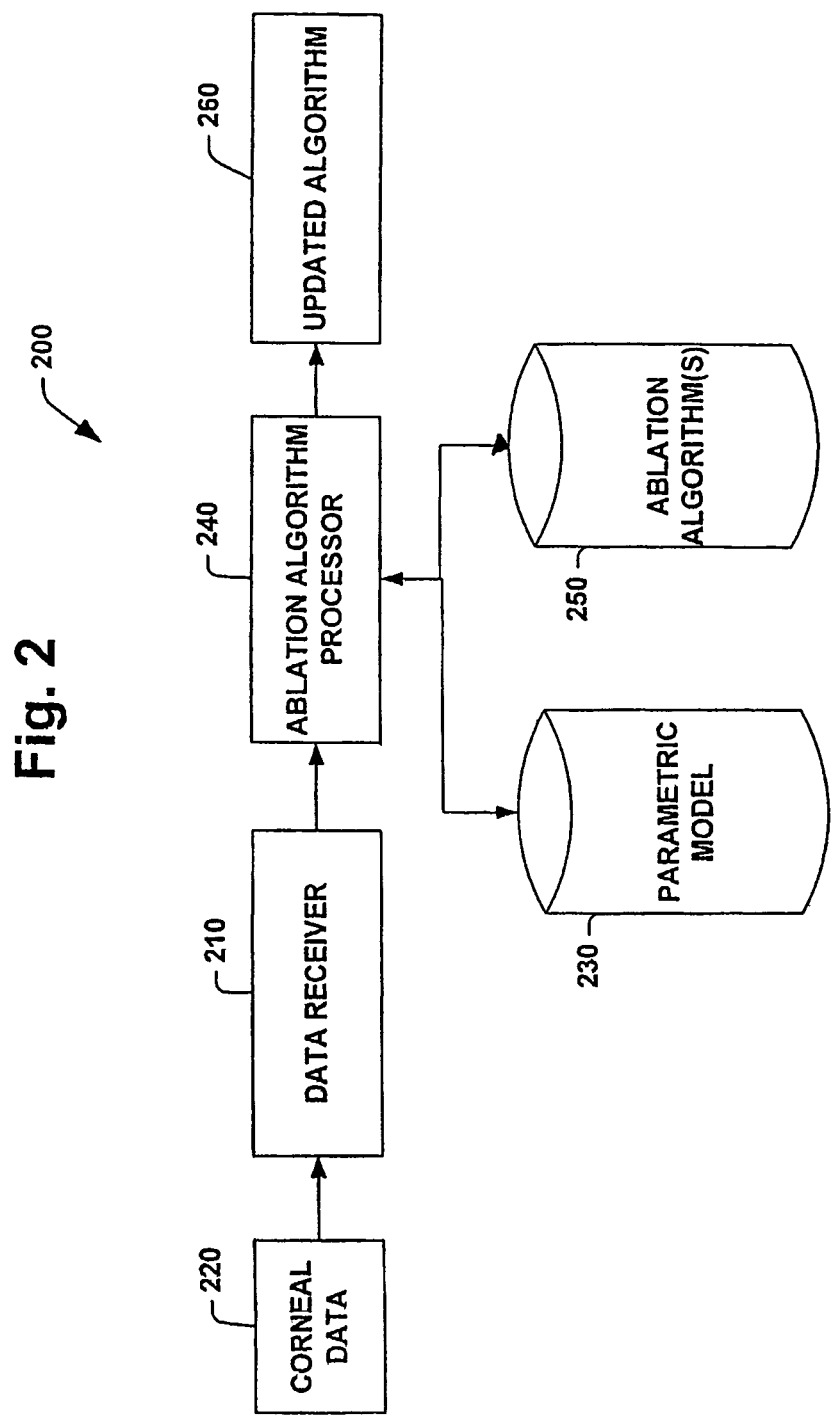
FIG. 2 illustrates an example parametric model system.

Turning now to FIG. 2, an example system 200 for updating a corneal ablation algorithm is illustrated. The system 200 includes a corneal data receiver 210 that receives corneal data 220. The corneal data receiver 210 can be, for example, a computer component. The corneal data 220 may be received, for example, via a computer communication. The corneal data 220 can include, but is not limited to, pre-operative measurements, measurements taken during surgery, and/or post-operative measurements. The corneal data 220 can include, for example, topographic data, pachymetric data, elevation data, total corneal thickness data, corneal curvature data, wave front data, intraocular pressure data, corneal acoustic response data, and so on. The corneal data 220 can also include measurements associated with one or more correlations like measurement pachymetry profile being correlated with post-operative result spherical aberration.

The system also includes a parametric model 230 that can be accessed by an ablation algorithm processor 240. The parametric model 230 can be stored, for example, in one or more data stores. By way of illustration, the parametric model 230 may be stored in one or more files, tables, hashes, lists, queues, state machines, data bases, and so on. The data store may reside in one computer component and/or be distributed between two or more communicating, co-operating computer components.

The parametric model 230 facilitates storing relations between one or more measurements, one or more predicted post-operative results, and one or more updates to a corneal ablative procedure. An example relation may take the form:

```
If m1 < v1 then
    por1 < r1
    thus
        aap1 = aap1 + u1
endif
``` where, m1 is a pre-operative measurement, v1 is a value for the pre-operative measurement, por1 is a predicted post-operative result, r1 is a value for the predicted post-operative result, aap1 is an ablation algorithm parameter and u1 is an update amount. u1 may be a pre-determined, configurable number and/or may be computed according to a formula that depends on one or more measurements like m1.

While the first example relation correlated one input measurement with one predicted post-operative result, it is to be appreciated that more than one input measurement may be related to a predicted post-operative result. Thus, another example relation may take the form:

```
If m1 in {a, b} and m2 in {c, d} then
    por2 < r2
    thus
        aap2 = aap2 + u2
else if m1 in {a, b} and m2 in {e, f} then
    por2 >= r2
    thus
        aap2 = aap2 - u2
end if
``` where m1 and m2 are pre-operative measurements, {a, b}, {c, d} and {e, f} are ranges of values for the pre-operative measurements, port is a predicted post-operative result, r2 is a value for the post-operative result, aap2 is an ablation algorithm parameter and u2 is an update amount. u2 may be a pre-determined, configurable value and/or may be the result of a function that depends on one or more input measurements like m1 and m2.

While the two example relations are described in a conditional language format, those skilled in the art will appreciate that the relations can be captured and stored in a variety of formats known in the art.

The ablation algorithm processor 240 analyzes the received corneal data 220 in light of the parametric model 230 and/or one or more correlations stored therein, and identifies ways in which an ablation algorithm can be updated. Thus, one or more ablation algorithms stored, for example, in an ablation algorithm data store 250 can be accessed by the ablation algorithm processor 240 and updated into an updated algorithm 260. The updated algorithm 260 can then be employed in ablation surgery.

While the system 200 is illustrated as a connected set of computer components, it is to be appreciated that some computer components may be integrated together into one or more computer components. Similarly, it is to be appreciated that all and/or part of the system 200 may itself be integrated into a surgical tool (e.g. laser system).

In another example, the system 200 may include a data integrator (not illustrated) that selectively updates the parametric model 230 based on data including, but not limited to, pre-operative data, pre-perturbation data, post-perturbation data, post-ablation data, post-operative data and results, and so on.

Additionally, and/or alternatively, the ablation algorithm processor 240 may initially select an algorithm from the ablation algorithm data store 250 based on the corneal data 220 and one or more correlations in the parametric model 230. For example, a first set of pre-operative measurement values may indicate that a first ablative algorithm that can be updated in a first set of ways be selected and then updated based on the first set of measurement values and one or more correlations. Similarly, a second set of pre-operative measurement values may indicate that a second ablative algorithm that can be updated in a second set of ways be selected and then updated based on the second set of measurement values and one or more correlations.

In view of the exemplary systems shown and described herein, example methodologies that are implemented will be better appreciated with reference to the flow diagrams of FIGS. 3, 4, 6, and 7. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Furthermore, additional and/or alternative methodologies can employ additional, not illustrated blocks. In one example, methodologies are implemented as computer executable instructions and/or operations, stored on computer readable media including, but not limited to an application specific integrated circuit (ASIC), a compact disc (CD), a digital versatile disk (DVD), a random access memory (RAM), a read only memory (ROM), a programmable read only memory (PROM), an electronically erasable programmable read only memory (EEPROM), a disk, a carrier wave, and a memory stick.

In the flow diagrams, rectangular blocks denote "processing blocks" that may be implemented, for example, in software. Similarly, the diamond shaped blocks denote "decision blocks" or "flow control blocks" that may also be implemented, for example, in software. Alternatively, and/or additionally, the processing and decision blocks can be implemented in functionally equivalent circuits like a digital signal processor (DSP), an application specific integrated circuit (ASIC), and the like.

A flow diagram does not depict syntax for any particular programming language, methodology, or style (e.g., procedural, object-oriented). Rather, a flow diagram illustrates functional information one skilled in the art may employ to program software, design circuits, and so on. It is to be appreciated that in some examples, program elements like temporary variables, routine loops, and so on are not shown.

Cutting the flap alters the corneal structure. Corneal measurements taken following cutting the corneal flap are therefore employed by some example methods and systems. As demonstrated above, the microkeratomic incision for the flap produces changes in the cornea. Since cutting the LASIK flap produces a response that facilitates predicting other responses, a method for customizing a refractive ophthalmic algorithm can include pre-operatively measuring the cornea, cutting the flap, measuring the cornea and/or the flap, and adjusting an ablation algorithm based on stored correlations between the measurements and predicted post-operative results.

Figure 3:
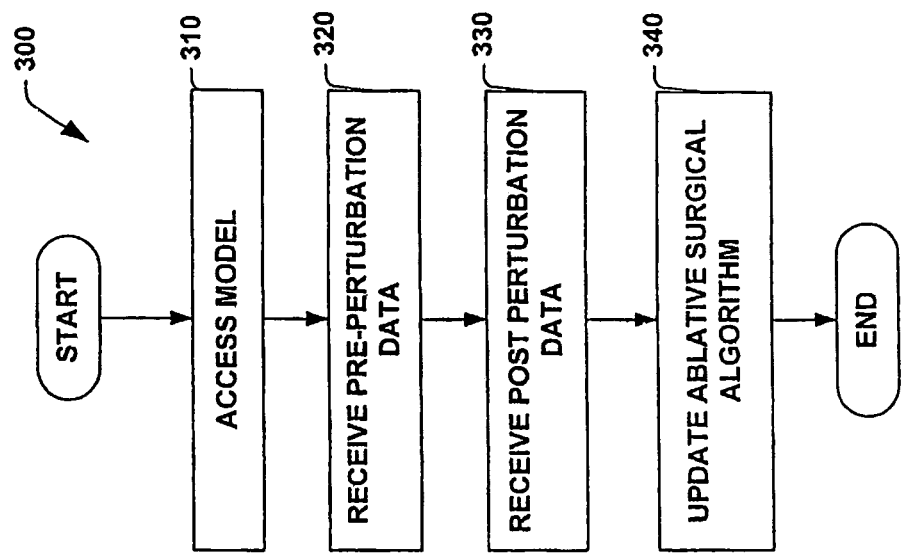
FIG. 3 illustrates an example parametric model method.

Turning now to FIG. 3, an example parametric model method 300 for selecting and/or updating an ablative algorithm is presented. At 310, a parametric model is accessed. For example, a data base query can be made, a table can be referenced, a data structure can be accessed, a file can be read, and so on. Data retrieved from the parametric model may, for example, identify candidate correlations and thus identify pre-perturbation data of interest to the method 300.

At 320, the method 300 receives a pre-perturbation data concerning a cornea on which a refractive ophthalmic treatment will be performed. The pre-perturbation data can include, but is not limited to, topographic data, pachymetric data, elevation data, corneal thickness data, corneal curvature data, corneal acoustic response and ultrasonic data, wave front data, and intraocular pressure data, where such data are associated with the cornea before it has been perturbed. The pre-perturbation may be associated with one or more correlations.

Thus, the method facilitates updating an ablative algorithm based on individual measurements before surgery. The measurements have been experimentally and statistically correlated with desired post-operative results. Example measurements include, but are not limited to, modulus of elasticity, corneal acoustic response to ultrasonic excitation, pachymetric profile in multiple meridians, pachymetric asymmetry between vertical and horizontal meridians, magnitude of difference in pachymetry between center and periphery, corneal width, anterior chamber angle and depth, corneal curvature profile in multiple meridians, magnitude of astigmatism, difference in astigmatism between center and periphery topographic response to the cutting of a LASIK flap. Example correlations include, but are not limited to, greater peripheral thickness causing greater spherical aberration. For example, measuring peripheral thickness facilitates predicting post-operative spherical aberration, thus a peripheral thickness measurement in the range {a, b} suggests taking action to increase peripheral ablation, diminishing post-operative spherical aberration. The perturbation can be, for example, a corneal incision, a corneal ablation, a LASIK flap cut, peeling the epithelial layer from the cornea, ultrasounds, and so on. In one embodiment, the perturbation causes the severing of corneal lamellae.

Thus, at 330, the method 300 receives a post-perturbation data. The post-perturbation data can include, but is not limited to, topographic data, pachymetric data, elevation data, total corneal thickness data, corneal curvature data, wave front data, corneal acoustic response and ultrasonic data, flap thickness data, and intraocular pressure data. The perturbation can be, for example, a corneal incision, a corneal ablation, a LASIK flap cut, an epithelial layer peel, and ultrasounds.

At 340, an ablative surgical algorithm is updated based, at least in part, on the pre-perturbation data, the post-perturbation data, and one or more correlations between one or more of the pre-perturbation data and a predicted post-operative result, the post-perturbation data and a predicted post-operative results, and/or the combination of the three.

The example method 300 thus relies on correlations between pre-perturbation data, post-perturbation data, and predicted post-operative results. For example, a pre-perturbation central flatness measurement, as related to a post-perturbation central flatness measurement may be correlated to a predicted post-operative central flatness result and thus an ablation depth may be updated in the ablation algorithm.

In an extension of method 300 (not illustrated), additional processing is undertaken. This additional processing includes receiving diagnostic data and selectively updating the parametric model based, at least in part, on the post-perturbation data and/or the diagnostic data. In this way, the parametric model can be updated over time to become more complete and thus provide even more accurate predictions. The diagnostic data can include, but is not limited to, corneal acoustic response and ultrasonic data, patient satisfaction data, patient visual acuity and visual performance data, patient halo effect and contour sensitivity data, topographic data, pachymetric data, elevation data, total corneal thickness data, corneal curvature data, wave front data, intraocular pressure data, flap thickness data, and refractive data.

In one example, the method 300 is run on a stand alone computer component that communicates via computer communications with a surgical laser. In another example, the method is run in a computer component located inside a surgical laser apparatus. In yet another example, portions of the method may run on a stand alone computer component while other portions of the method may run in a computer component located inside a surgical laser apparatus, with the two portions of the method communicating via a computer communication.

Turning now to FIG. 4, an example corneal ablative surgical method 400 is illustrated. The method 400 includes, at 410, measuring a first set of corneal measurements. These measurements are taken before any corneal lamellae are severed. The measurements can include, but are not limited to, corneal acoustic response and ultrasound data, topographic data, pachymetric data, elevation data, corneal thickness data, corneal curvature data, wave front data, intraocular pressure data, peripheral stroma thickness data, an age datum, a sex datum, years of contact lens use data, and prior surgical response data and can be acquired by one or more of corneal topography, optical coherence tomography, wave front analysis, ultrasound, and patient interview.

At 420, based on the data acquired at 410, a corneal ablative algorithm is selectively updated. For example, portions of the algorithm may be enhanced, other portions may be diminished, some may be added, and others may be deleted. Furthermore, an algorithm may initially be chosen based on the data acquired at 410, and then the chosen algorithm may be updated. The choice of an algorithm and its selective updating are based, at least in part, on one or more correlations between the data acquired at 410 and one or more desired post-operative results, where the correlations are stored in a parametric model.

At 430, the surgical method includes severing one or more corneal lamellae. The severing can occur as the result of, for example, cutting a LASIK flap, corneal scraping, ablation, epithelial peeling, and the like. In another example, where the surgical method is performed by a surgical apparatus and the method 400 is in operable and/or data communication with the surgical apparatus, the method 400 may not include severing the corneal lamellae. Rather, the method 400 would be confined to performing the algorithm updating based on the measurements and correlations. Thus, rather than being a surgical method, the alternate method would be a surgical support method.

At 440, measuring a second set of corneal measurements occurs. These measurements are taken after one or more corneal lamellae are severed. The measurements can include, but are not limited to, corneal acoustic response and ultrasound data, topographic data, pachymetric data, elevation data, corneal thickness data, corneal curvature data, wave front data, intraocular pressure data, peripheral stroma thickness data, an age datum, a sex datum, years of contact lens use data, and prior surgical response data and can be acquired by one or more of corneal topography, optical coherence tomography, wave front analysis, ultrasound, and patient interview.

At 450, the method includes selectively updating the ablation algorithm based on the second set of corneal measurements and one or more correlations between the measurements and post-operative results stored in a parametric model. Additionally, and/or alternatively, the correlations may relate the first set of corneal measurements and the second set of corneal measurements with desired post-operative results and suggested algorithm updates.

At 460, the surgical method 400 includes ablating corneal tissue according to the updated algorithm. In one example, the method 400 is run on a stand alone computer component that communicates via computer communications with a surgical laser. In another example, the method 400 is run in a computer component located inside a surgical laser apparatus. In yet another example, portions of the method 400 may run on a stand alone computer component while other portions of the method may run in a computer component located inside a surgical laser apparatus, with the two portions of the method 400 communicating via a computer communication. In another example, where the surgery is performed by a person and/or apparatus in operable and/or data communication with the method 400, then the method 400 may not include 460, this act being performed by an entity related to but not part of the method. Thus, the method 400 would be a surgical support method rather than a surgical method.

In an example method, corneal measurements are taken by methods including, but not limited to, corneal topography, optical coherence tomography, ultrasound (including high frequency ultrasound), refraction, and/or wave front analysis. These measurements are taken before and after the microkeratomic incision for the corneal flap. Ablation algorithm adjustments can thus be made in advance of the ablation in a separate procedure and/or in real time as an intraoperative adjustment after the perturbation (e.g., cut, ablation) but before the ablation.

Example correlations concern factors including, but not limited to, Young's modulus, age, sex, race, years of contact lens wear, thickness, curvature, and corneal size. For example, corneas of older individuals tend to be stiffer than those of younger individuals. Thus, myopic procedures generally apply less ablation to older corneas to achieve the same level of correction.

Regression analysis between central curvature change and peripheral elevation change from thirty subjects who underwent LASIK procedures demonstrated a positive correlation ($R^2$=0.56, p<0.0001) indicating that the greater the increase in elevation outside the ablation zone, the greater the flattening curvature change centrally. Thus, this application describes example systems and methods that are adapted based on pre-operative measurements and/or measurements taken during a surgical procedure, based, at least in part, on this and/or other determined correlations. The correlations can be stored, for example, in a parametric model.

In one case study, regression analysis of central curvature versus peripheral stromal thickness was performed. The plots of this analysis are illustrated in FIG. 5. Central curvature has a negative correlation with peripheral thickness, both inferior and superior, meaning the greater the peripheral thickness, the flatter the central curvature. FIG. 5 illustrates a regression analysis of peripheral stromal thickness of the superior region (left) and inferior region (right) against curvature in the central 3 mm region, pre-operatively and at 4 time points post-operatively after PRK in one patient. This demonstrates how central curvature for this patient closely tracked peripheral stromal thickness over time. Thus, the application describes example systems and methods that are customizable based on pre-operative measurements and/or measurements taken during surgery based, at least in part, on correlations associated with peripheral stromal thickness.

Turning now to FIG. 6, an example corneal ablative algorithm updating method 600 is illustrated. This example method does not employ measurements taken during surgery. Thus, method 600 may be employed, for example, in LASEK and PRK. Additionally, it could be employed in LASIK surgery. The method 600 includes, at 610, accessing a parametric model that stores one or more correlations between pre-operative measurements and post-operative results, which facilitates retrieving and/or generating updates to an ablative algorithm. The correlations are associated with suggested adaptations to ablative algorithms. In one example, the correlations are associated with suggestions for choosing an ablative algorithm that may then be customized based on pre-operative measurements.

At 620, pre-operative data is received. The data can include, but is not limited to, patient visual acuity and visual performance data, corneal acoustic response and ultrasound data, topographic data, pachymetric data, elevation data, corneal thickness data, corneal curvature data, wave front data, intraocular pressure data, peripheral stroma thickness data, an age datum, a sex datum, years of contact lens use data, and a prior surgical response data and can be acquired by one or more of patient questioning, corneal topography, optical coherence tomography, wave front analysis, ultrasound, and patient interview.

At 630, based on the pre-operative data and one or more correlations relating one or more pieces of pre-operative data and predicted post-operative results, a corneal ablative algorithm can be updated. For example, measuring peripheral thickness facilitates predicting post-operative spherical aberration, thus a peripheral thickness measurement in the range {a, b} suggests taking action to increase peripheral ablation, diminishing post-operative spherical aberration. While a one to one correlation is described, it is to be appreciated that two or more pieces of pre-operative data can be related to one or more predicted post-operative results.

In one example, the method 600 is complete at 630. But in another example, the method 600 includes, at 640, ablating tissue in accordance with the updated ablative algorithm. In one example, the method 600 is run on a stand-alone computer component that communicates via computer communications with a surgical laser. In another example, the method 600 is run in a computer component located inside a surgical laser apparatus. In yet another example, portions of the method 600 may run on a stand alone computer component while other portions of the method 600 may run in a computer component located inside a surgical laser apparatus, with the two portions of the method 600 communicating via a computer communication.

Turning now to FIG. 7, a method 700 for updating an algorithm is illustrated. The method 700 does not include performing surgery, rather it concerns updating an algorithm that is employed during surgery. Thus, the method 700 may be run remotely from the surgery. For example, a surgeon with a laser surgical tool may be located in a remote location (e.g., hospital overseas). The patient can benefit from processing performed remotely (e.g., hospital in U.S.) by method 700. Thus, the method 700 and the surgeon and/or laser surgical tool may be in data communication via computer communications. For example, data packets carrying data and/or carrier waves carrying computer executable instructions may pass between the method 700 and the surgeon and/or laser. Similarly, other example methods and systems described herein may engage in similar data transfer and/or instruction transfer.

At 710, the method 700 access a model 710 that stores correlations between pre-perturbation data and predicted post-operative results. At 720, pre-perturbation data is received. Based on the data received, its values, and one or more correlations between the data, its values, and a predicted post-operative result(s), at 730, an ablative algorithm is updated. For example, the pre-perturbation data may be related to a post-operative result in a manner that suggests that additional ablation in an additional zone should be undertaken. Thus, an ablation algorithm can be suitably updated. For example, an additional record in a database of locations to be ablated could be added, instructions for ablating to a certain depth could be added to an algorithm, timing instructions could be updated, pre-determined, configurable data values and/or limits could be manipulated, and so on.

At 740, post-perturbation data is received. Then, at 750, based on a correlation(s) between the post-perturbation data and predicted post-operative results, the ablative algorithm can be updated again. Additionally, and/or alternatively, a correlation between pre-perturbation data, post-perturbation data, and a predicted post-operative result can identify algorithm updates.

Those skilled in the art of computer programming, mathematical computer modeling, and/or data base manipulation and administration will readily appreciate that example systems and methods described herein may be embodied in software and/or one or more computer components. Thus, FIG. 8 illustrates a computer 800 that includes a processor 802, a memory 804, a disk 806, input/output ports 810, and a network interface 812 operably connected by a bus 808. Executable components of systems described herein may be located on a computer like computer 800. Similarly, computer executable methods described herein may be performed on a computer like computer 800. It is to be appreciated that other computers may also be employed with the systems and methods described herein.

The processor 802 can be a variety of various processors including dual microprocessor and other multi-processor architectures. The memory 804 can include volatile memory and/or non-volatile memory. The non-volatile memory can include, but is not limited to, read only memory (ROM), programmable read only memory (PROM), electrically programmable read only memory (EPROM), electrically erasable programmable read only memory (EEPROM), and the like. Volatile memory can include, for example, random access memory (RAM), synchronous RAM (SRAM), dynamic RAM (DRAM), synchronous DRAM (SDRAM), double data rate SDRAM (DDR SDRAM), and direct RAM bus RAM (DRRAM). The disk 806 can include, but is not limited to, devices like a magnetic disk drive, a floppy disk drive, a tape drive, a Zip drive, a flash memory card, and/or a memory stick. Furthermore, the disk 806 can include optical drives like, compact disk ROM (CD-ROM), a CD recordable drive (CD-R drive), a CD rewriteable drive (CD-RW drive) and/or a digital versatile ROM drive (DVD ROM). The memory 804 can store processes 814 and/or data 816, for example. The disk 806 and/or memory 804 can store an operating system that controls and allocates resources of the computer 800.

The bus 808 can be a single internal bus interconnect architecture and/or other bus architectures. The bus 808 can be of a variety of types including, but not limited to, a memory bus or memory controller, a peripheral bus or external bus, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus.

The computer 800 interacts with input/output devices 818 via input/output ports 810. Input/output devices 818 can include, but are not limited to, a keyboard, a microphone, a pointing and selection device, cameras, video cards, displays, and the like. The input/output ports 810 can include but are not limited to, serial ports, parallel ports, and USB ports.

The computer 800 can operate in a network environment and thus is connected to a network 820 by a network interface 812. Through the network 820, the computer 800 may be logically connected to a remote computer 822. The network 820 includes, but is not limited to, local area networks (LAN), wide area networks (WAN), and other networks. The network interface 812 can connect to local area network technologies including, but not limited to, fiber distributed data interface (FDDI), copper distributed data interface (CDDI), ethernet/IEEE 802.3, token ring/IEEE 802.5, and the like. Similarly, the network interface 812 can connect to wide area network technologies including, but not limited to, point to point links, and circuit switching networks like integrated services digital networks (ISDN), packet switching networks, and digital subscriber lines (DSL).

Pre-operative, postoperative and during surgery measurements can be input to one or more computer components by methods including, but not limited to, key stroke, direct data transfer, and so on. During corneal ablative surgery, the methods described herein may be performed on a computer system with which a surgical team member communicates. Data may be input to the computer during the surgical process. The method can then update the algorithm that is employed in subsequent steps of the surgery.

The systems, methods, data structures, models and objects described herein may be stored, for example, on a computer readable media. Media can include, but are not limited to, an application specific integrated circuit (ASIC), a compact disc (CD), a digital versatile disk (DVD), a random access memory (RAM), a read only memory (ROM), a programmable read only memory (PROM), a disk, a carrier wave, a memory stick, and the like. Thus, an example computer readable medium can store computer executable instructions for the methods claimed herein and equivalents thereof.

Referring now to FIG. 9, an application programming interface (API) 900 is illustrated providing access to a system 910 for ablative algorithm updating. The API 900 can be employed, for example, by programmers 920 and/or processes 930 to gain access to processing performed by the system 910. For example, a programmer 920 can write a program to access the system 910 (e.g., to invoke its operation, to monitor its operation, to access its functionality) where writing a program is facilitated by the presence of the API 900. Thus, rather than the programmer 920 having to understand the internals of the system 910, the programmer's task is simplified by merely having to learn the interface to the system 910. This facilitates encapsulating the functionality of the system 910 while exposing that functionality. Similarly, the API 900 can be employed to provide data values to the system 910 and/or retrieve data values from the system 910.

For example, a process 930 that retrieves corneal measurements can provide the corneal measurements to the system 910 and/or the programmers 920 via the API 900 by, for example, using a call provided in the API 900. Thus, in one example of the API 900, a set of application program interfaces can be stored on a computer-readable medium. The interfaces can be executed by a computer component to gain access to a system for ablative algorithm updating. Interfaces can include, but are not limited to, a first interface 940 that facilitates communicating measurement data associated with corneal ablative surgery, a second interface 950 that facilitates communicating correlation data associated with ablative algorithm updating, and a third interface 960 that facilitates communicating algorithm updating data and/or instructions generated from the measurement data and the correlation data by the algorithm updater 910.

Referring now to FIG. 10, information can be transmitted between various computer components associated with ablative algorithm updating described herein via a data packet 1000. An exemplary data packet 1000 is shown. The data packet 1000 includes a header field 1010 that includes information such as the length and type of packet. A source identifier 1020 follows the header field 1010 and includes, for example, an address of the computer component from which the packet 1000 originated. Following the source identifier 1020, the packet 1000 includes a destination identifier 1030 that holds, for example, an address of the computer component to which the packet 1000 is ultimately destined. Source and destination identifiers can be, for example, globally unique identifiers (guids), URLS (uniform resource locators), path names, and the like. The data field 1040 in the packet 1000 includes various information intended for the receiving computer component. The data packet 1000 ends with an error detecting and/or correcting 1050 field whereby a computer component can determine if it has properly received the packet 1000. While six fields are illustrated in the data packet 1000, it is to be appreciated that a greater and/or lesser number of fields can be present in data packets.

FIG. 11 is a schematic illustration of sub-fields 1100 within the data field 1040 (FIG. 10). The sub-fields 1100 discussed are merely exemplary and it is to be appreciated that a greater and/or lesser number of sub-fields could be employed with various types of data germane to ablative algorithm updating. The sub-fields 1100 include a field 1110 that stores information concerning measurement data (e.g., pre-perturbation, post-perturbation) and a second field 1120 that stores a correlation data relating the measurement data to a predicted post-operative result. The sub-fields 1100 may also include a field 1130 that stores an algorithm update data computed in response to the measurement data 1110 and the correlation data 1120.

What has been described above includes several examples. It is, of course, not possible to describe every conceivable combination of components or methodologies for purposes of describing the methods, systems, computer readable media and so on employed in updating an ablative algorithm. However, one of ordinary skill in the art may recognize that further combinations and permutations are possible. Accordingly, this application is intended to embrace alterations, modifications, and variations that fall within the scope of the appended claims. Furthermore, to the extent that the term "includes" is employed in the detailed description or the claims, it is intended to be inclusive in a manner similar to the term "comprising" as that term is interpreted when employed as a transitional word in a claim.

The invention claimed is:

1. A parametric model-based computer implemented method for customizing an ablative surgical algorithm for use in refractive ophthalmic surgery, comprising:
   receiving, with a data receiver of a computer, at least two types of pre-perturbation data pertaining to a cornea on which a refractive ophthalmic surgery will be performed, wherein pre-perturbation data is empirical data acquired before a perturbation of said cornea, said perturbation inducing a biomechanical response;
   receiving, with a data receiver of the computer, at least two types of post-perturbation data pertaining to said cornea, the post-perturbation data being empirical data acquired after a perturbation of said cornea; wherein the post-perturbation data types received are the same as the pre-perturbation data types received;
   accessing, with a processor of the computer, a parametric model stored in a computer readable medium, the parametric model storing one or more correlations between measured corneal data and post-operative results pertaining to a plurality of corneas on which refractive ophthalmic surgeries were previously performed, such measured data at least being of the same types as the pre-perturbation and post-perturbation data types;
   predicting, with a processor of the computer, a post-operative result for said cornea using the parametric model, the pre-perturbation data received, and the post-perturbation data received; and
   selectively updating, with a processor of the computer, an ablative surgical algorithm stored in a computer readable medium, the updating based, at least in part, on the predicted post-operative result, the pre-perturbation data, and the post-perturbation data;
   wherein the updated surgical algorithm is customized for the cornea on which a refractive ophthalmic surgery will be performed.

2. The method of claim 1, wherein the pre-perturbation and post-perturbation data types received are selected from topographic data, pachymetric data, elevation data, corneal thickness data, corneal curvature data, corneal acoustic response and ultrasonic data, wave front data, intraocular pressure data, peripheral stromal thickness data.

3. The method of claim 2, wherein the pre-perturbation data received is acquired by one or more of corneal topography, optical coherence tomography, wave front analysis, ultrasound, and patient interview.

4. The method of claim 2, further comprising receiving, with a data receiver of a computer, other patient data selected from one or more of age data, sex data, contact lens data, prior surgical response data, patient visual acuity and visual performance data.

5. The method of claim 1, wherein the measured data types are selected from topographic data, pachymetric data, elevation data, corneal thickness data, corneal curvature data, corneal acoustic response and ultrasonic data, wave front data, flap thickness data, intraocular pressure data, peripheral stromal thickness data, age data, sex data, contact lense data, prior surgical response data, patient visual acuity and visual performance data.

6. The method of claim 5, wherein the post-perturbation data received is acquired by one or more of corneal topography, optical coherence tomography, wave front analysis, ultrasound, and patient interview.

7. The method of claim 1 implemented in a computer data signal embodied in a transmission medium, comprising:
   a first set of instructions for receiving corneal data selected from one or more of the pre-perturbation data and the post-perturbation data;
   a second set of instructions for selectively updating an ablative algorithm based upon one or more correlations between the corneal data and a post-operative result, the correlations being stored in a parametric model and associated with suggested adaptations to the ablative algorithm; and
   a third set of instructions for updating the ablative algorithm based on the corneal data and the one or more correlations.

8. The method of claim 1, comprising:
   storing in a memory of a laser eye surgery apparatus an ablation program that controls a laser of the apparatus for ablating corneal tissue;
   storing in the memory corneal data selected from one or more of the pre-perturbation data and the post-perturbation data;
   storing in the memory the parametric model that stores a correlation between the corneal data and the post-operative result;
   adapting with a processor of the apparatus the ablation program based on the correlation; and
   storing in the memory the adapted ablation program.

9. The method of claim 1, comprising ablating corneal tissue from a cornea in accordance with the updated corneal ablative algorithm.

10. The method of claim 9 implemented in a system for updating the parametric model, comprising:
- a data receiver for receiving at least one of the pre-perturbation data, the post-perturbation data, a post-ablation data concerning the cornea on which the refractive opthalmic surgery was performed, and a patient visual performance data concerning the cornea on which the refractive opthalmic surgery was performed; and
- a data integrator that selectively updates the parametric model based, at least in part, on at least one of, the pre-perturbation data, the post-perturbation data, the post-ablation data, and the patient visual performance data.

11. The method of claim 1, wherein updating of the ablative surgical algorithm is based on (i) the pre-perturbation data and one or more correlations between the pre-perturbation data and one or more post-operative results of corneas on which refractive ophthalmic surgeries were previously performed; and (ii) the post-perturbation data and one or more correlations between the post-perturbation data and one or more post-operative results of corneas on which refractive ophthalmic surgeries were previously performed.

12. A computer readable medium storing computer executable instructions operable to perform computer executable portions of a method for customizing an ablative surgical algorithm for use in refractive ophthalmic surgery, comprising:
  receiving, with a data receiver of a computer, at least two types of pre-perturbation data pertaining to a cornea on which a refractive ophthalmic surgery will be performed, wherein pre-perturbation data is empirical data acquired before a perturbation of said cornea, said perturbation inducing a biomechanical response;
  receiving, with a data receiver of the computer, at least two types of post-perturbation data pertaining to said cornea, the post-perturbation data being empirical data acquired after a perturbation of said cornea; wherein the post-perturbation data types received are the same as the pre-perturbation data types received;
  accessing, with a processor of the computer, a parametric model stored in a computer readable medium, the parametric model storing one or more correlations between measured corneal data and post-operative results pertaining to a plurality of corneas on which refractive ophthalmic surgeries were previously performed, such measured data at least being of the same types as the pre-perturbation and post-perturbation data types;
  predicting, with a processor of the computer, a post-operative result for said cornea using the parametric model, the pre-perturbation data received, and the post-perturbation data received; and
  selectively updating, with a processor of the computer, an ablative surgical algorithm stored in a computer readable medium, the updating based, at least in part, on the predicted post-operative result, the pre-perturbation data, and the post-perturbation data;
  wherein the updated surgical algorithm is customized for the cornea on which a refractive ophthalmic surgery will be performed.

* * * * *